(12) United States Patent
Penades et al.

(10) Patent No.: US 7,364,919 B2
(45) Date of Patent: Apr. 29, 2008

(54) NANOPARTICLES

(75) Inventors: Soledad Penades, Seville (ES); Javier Rojo, Seville (ES); Manuel Martin-Lomas, Seville (ES)

(73) Assignee: Midatech Limited, Abingdon, Oxfordshire (GB)

( * ) Notice: Subject to any disclaimer, the term of this patent is extended or adjusted under 35 U.S.C. 154(b) by 535 days.

(21) Appl. No.: 10/399,284

(22) PCT Filed: Oct. 16, 2001

(86) PCT No.: PCT/GB01/04633

§ 371 (c)(1),
(2), (4) Date: Oct. 29, 2003

(87) PCT Pub. No.: WO02/32404

PCT Pub. Date: Apr. 25, 2002

(65) Prior Publication Data

US 2004/0052729 A1    Mar. 18, 2004

(30) Foreign Application Priority Data

Oct. 16, 2000    (GB)    ................................. 0025414.4

(51) Int. Cl.
  *G01N 33/551*    (2006.01)
  *G01N 33/552*    (2006.01)
  *G01N 33/553*    (2006.01)

(52) U.S. Cl. .................... 436/524; 435/6; 436/525; 436/527; 436/173

(58) Field of Classification Search .................... None
See application file for complete search history.

(56) References Cited

U.S. PATENT DOCUMENTS 4,313,734 A * 2/1982 Leuvering ................... 436/525

5,248,772 A  9/1993 Siiman et al. ............... 536/112
5,766,572 A  6/1998 Hasegawa et al. ........ 424/9.322
6,132,750 A  10/2000 Perrier et al. ................ 424/418

FOREIGN PATENT DOCUMENTS

| | | |
|---|---|---|
| EP | 0 465 081 | 1/1992 |
| FR | 2 777 193 | 4/1998 |
| WO | WO83/00173 | 5/1983 |
| WO | WO89/03675 | 5/1989 |
| WO | WO95/31220 | 11/1995 |
| WO | WO 99/61911 | 12/1999 |

OTHER PUBLICATIONS

WPI Accession No. 1996-010697/01 (Abstract).
Ada, "Vaccines and Vaccination", N. Engl. J. Med., vol. 345, No. 14, pp. 1042-1053 (2001).

(Continued)

*Primary Examiner*—Christopher L. Chin
(74) *Attorney, Agent, or Firm*—Edwards Angell Palmer & Dodge LLP; Peter C. Lauro, Esq.

(57) ABSTRACT

Materials and methods for studying and modulating the interaction of carbohydrate-containing moieties with other species are described, in particular, small particles, e.g. clusters of metal or semiconductor atoms, which can be employed as a substrate for immobilizing a plurality of ligands comprising carbohydrate groups. These "nanoparticles" can then be used to study carbohydrate mediated interactions, e.g. with other carbohydrates or proteins, and as therapeutics and diagnostic reagents.

32 Claims, 3 Drawing Sheets

OTHER PUBLICATIONS

Boal, et al., "Self-assembly of nanoparticles into structures spherical and network aggregates"; Nature. vol. 404, pp. 746-748 (2000).

Brown and London, "Structure of Detergent-Resistant Membrane Domains: Does Phase Separation Occure in Biological Membranes?", Biochemical and Biophysical Research Communications, 240, pp. 1-7 (1997).

Brust, et al., "Synthesis and Reactions of Functionalised Gold Nanoparticles"; J. Chem Soc., Chem. Commun., pp. 1655-1656 (1995).

Coteron, et al., "Glycophanes, Cyclodextrin-Cyclophane Hybrid Receptors for Apolar Binding in Aqeous Solutions. A Stereoselective Carbohydrate-Carbohydrate interaction in Water"; J. Am. Chem. Soc., vol. 115, No. 22, pp. 10066-10076 (1993).

Eggens, et al., "Specific Interacton between $Le^x$ and $Le^x$ Determinants", The Journal of Biological Chemistry, vol. 264, No. 16, pp. 9476-9484 (1989).

Fitzmaurice, et al., "Heterosupramolecular Chemistry: Programmed Pseudorotaxane Assembly at the Surface of a Nanocrystal", Angew. Chem. Int. Ed. vol. 38, No. 8, pp. 1147-1150 (1999).

Frey, et al., "Role of the Glycocalyx in Regulating Access of Microparticles to Apical Plasma Membranes of Intestinal Epithelial Cells: Implications for Microbial Attachment and Oral Vaccine Targeting", J. Exp. Med., vol. 184, pp. 1045-1059 (1996).

Hakomori, "Carbohydrate-carbohydrate interaction as an initial step in cell recognition", Pure & Appl. Chem., vol. 63, No. 4, pp. 473-482 (1991).

Hakomori, et al., "New insights in glycosphingolipid function: 'glycosignaling domain,' a cell surface assembly of glycosphingolipids with signal transducer molecules, involved in cell adhesion coupled with signaling", Glycobiology, vol. 8, No. 10, pp. xi-xix (1998).

Horan, et al., "Nonstatistical binding of a protein to clustered carbohydrates", PNAS, vol. 96, No. 21, pp. 11782-11786 (1999).

Jiménez-Barbero, et al., "Molecular Recognition of Carbohydrates Using a Synthetic Receptor. A Model System To Understand the Stereoselectivity of a Carbohydrate-Carbohydrate Interaction in Water", J. Am. Chem. Soc., vol. 117, No. 45, pp. 11198-11204 (1995).

Kiessling and Pohl, "Strength in numbers: non-natural polyvalent carbohydrate derivatives", Chemistry & Biology, vol. 3, No. 2, pp. 71-77 (1996).

Nitov, et al., "Shiga-like toxins are neutralized by tailored multivalent carbohydrate ligands", Nature, vol. 403, pp. 669-672 (2000).

Klarreich, "Biologists join the dots", Nature, vol. 413, pp. 450-452 (2001).

Liang, et al., "Polyvalent binding to carbohydrates immobilized on an insoluble resin", Proc. Natl. Acad. Sci. USA, vol. 94, pp. 10554-10559 (1997).

Liu, et al., "Cyclodextrin-Modified Gold Nanospheres. Host-Guest Interactions at Work to Control Colloidal Properties", J. Am. Chem. Soc., vol. 121, pp. 4304-4305 (1999).

Mammen, et al., "Polyvalent Interactions in Biological Systems: Implications for Design and Use of Multivalent Ligands and Inhibitors", Angew. Chem. Int. Ed., vol. 37, pp. 2754-2794 (1998).

Misevic, "Molecular Self-Recognition and Adhesion via Proteoglycan to Proteoglycan Interactions as a Pathyway to Multicellularity: Atomic Force Microscopy and Color Coded Bead Measurements in Sponges", Microscopy Research and Technique, vol. 44, pp. 304-309 (1999).

Morales, et al., "Carbohydrate-Carbohydrate Interactions in Water with Glycophanes as Model Systems", J. Org. Chem. vol. 63, pp. 9212-9222 (1998).

Nilsson and Mandenlus, "A Carbohydrate Biosensor Surface for the Detection of Uropathogenic Bacteria", Bio/Technology, vol. 12, pp. 1376-1378 (1994).

Revell, et al., "Self-Assembled Carbohydrate Monolayers: Formation and Surface Selective Molecular Recognition", Langmuir, vol. 14, pp. 4517-4524 (1998).

Schmidt and Jung, "Oligosaccharide Synthesis with Trichloroacetimidates", pp. 283-312.

Simons and Ikonen, "Functional rafts in cell membrances", Nature, vol. 387, pp. 569-572 (1997).

Storhoff and Mirkin, "Programmed Materials Synthesis with DNA", Chem. Rev., vol. 99, No. 7, pp. 1849-1862 (1999).

Strömberg, et al., "Saccharide orientation at the cell surface affects glycolipid receptor function", Proc. Natl. Acad. Sci. USA, vol. 88, pp. 9340-9344 (1991).

Taton, et al., "Scanometric DNA Array Detection with Nanoparticle Probes", Science, vol. 289, pp. 1757-1760 (2000).

Templeton, et al., "Monolayer-Protected Cluster Molecules", Acc. Chem. Res., vol. 33, No. 1, pp. 27-36 (2000).

Templeton, et al., "Water-Soluble, Isolable Gold Clusters Protected by Tiopronin and Coenzyme A Monolayers", Langmuir, vol. 15, pp. 66-76 (1999).

Weigel, et al., "Adhesion of Hepatocytes to Immobilized Sugars", Journal of Biological Chemistry, vol. 254, No. 21, pp. 10830-10838 (1979).

Weis and Drickamer, "Structural basis of lectin-carbohydrate recognition", Annu. Rev. Biochem., vol. 65, pp. 441-473 (1996).

Zutshi, et al., Inhibiting the assembly of protein-protein interfaces, Current Opinion in Chemical Biology, vol. 2, pp. 62-66 (1998).

Moore et al., "Tumoral Distribution of Long-Circulating Dextran-Coated Iron Oxide Nanoparticles in a Rodent Model", Radiology 2000 United States, vol. 214, No. 2, 2000, pp. 568-574.

European Search Report (Re: EP 05 02 6069).

Tromas, C., et al. "Adhesion Forces Between Lewis Determinant Antigens AsMeasured By Atomic Force Microscopy", Angew. Chem. Int. Ed. 2001, 40, No. 16, pp. 3052-3055, May 5, 2001.

de la Fuente, et al. "Gold Glyconanoparticles As Water-Soluble Polyvalent Models To Study Carbohydrate Interactions", Angew. Chem. Int. Ed. 2001, 40, No. 12, pp. 2258-2261, Jan. 19, 2001.

Bell G.I., et al. "Cell Adhesion: Competition Between Nonspecific Repulsion and Specific Binding." *Biophys. J* 45: 1051-1064 (1984).

Houseman B.T., et al. "The Role of Ligand Density in the Enzymatic Glycosylation of Carbohydrates Presented on Self-Assembely Mononlayers of Alkanethiolates on Gold." *Angew. Chem. Int. Ed.* 38(6): 782-785 (1999).

Yarema K.J., et al., "Chemical Approaches to Glycobiology and Emerging Carbohydrate-Based Therapeutic Agents." *Curr. Opin. Chem. Biol.* 2(1): 49-61 (1998).

\* cited by examiner

NANOPARTICLES

This application is a U.S. national phase application, pursuant to 35 U.S.C. §371, of PCT international application Ser. No. PCT/GB01/04633, filed Oct. 16, 2001, designating the United States, and published in English as international publication WO 02/32404 A2 on Apr. 25, 2002, which claims priority to GB application Ser. No. 0025414.4, filed Oct. 16, 2000.

FIELD OF THE INVENTION

The present invention relates to nanoparticles, and in particular to nanoparticles having immobilised ligands comprising carbohydrate groups and their use in studying the interaction of these ligands with other species. The present invention further relates to applications of the nanoparticles, for example for screening, diagnosis and therapy.

BACKGROUND OF THE INVENTION

There are three major classes of biopolymers, nucleic acid, proteins and carbohydrates. Protein and nucleic acid structure and interactions have been extensively studied in the art and the template-driven nature of protein and nucleic acid synthesis and the fact that these polymers are linear has meant that the techniques for their production and study have now been largely automated.

However, carbohydrates and their interactions with other species are also extremely important biologically and have not been the subject of concerted study. The difficulty in studying carbohydrates and their interactions arises in view of the diversity of carbohydrate linkages and because there are no techniques analogous to cloning to amplify and modify carbohydrates. On the contrary, the complex multistep way in which carbohydrates are assembled in cells means that carbohydrates and associated glycoconjugates such as glycoproteins and glycolipids are characterised by a high degree of variability and are not trivial to synthesise or study. In addition, carbohydrate mediated interactions tend to be weak and polyvalent and are correspondingly difficult to detect. Thus, there are no satisfactory tools for doing this in the art.

However, despite these characteristics, carbohydrate mediated interactions are important biologically. The surfaces of most types of cells are covered with a dense coating of glycoconjugates given rise to the so-called glycocalyx. It is believed that the glycocalyx is responsible for the repulsive forces which prevent non-specific adhesion of cells. However, in some cell configurations the repulsive barrier will be counterbalanced by the formation of cell-cell contacts through attractive forces.[1] There is now evidence that beside the well-known carbohydrate-protein interactions,[2] cells use attractive interactions between surface carbohydrates as a novel mechanism for cell adhesion and recognition.[3] A characteristic feature of these interactions is its low affinity that is compensated by a polyvalent presentation of ligands and receptors at the cell surfaces.[4]

Investigations into polyvalent carbohydrate-protein interactions have been approached using different multivalent carbohydrate model systems.[5] Examples of prior art approaches include the use of two dimensional arrays of glycoconjugates on gold surfaces[6a], the use of liposomes to display carbohydrates, dendrimer technology, and the use of polymers to provide linear and spherical carbohydrate arrays[5a, b]. However, the problems of studying interactions involving carbohydrates are far from solved and there is a continuing need in the art for new methods and tools for doing this.

SUMMARY OF THE INVENTION

Broadly, the present invention provides materials and methods for studying and modulating the interaction of carbohydrate-containing moieties with other species. In particular, the present invention provides small particles, e.g. clusters of metal or semiconductor atoms, which can be employed as a substrate for immobilising a plurality of ligands, the ligands comprising carbohydrate groups. These 'nanoparticles' can then be used to study carbohydrate mediated interactions, e.g. with other carbohydrates or proteins, and as therapeutics and diagnostic reagents. Thus, the present invention provides a way of providing a spherical array of the ligand immobilised on a detectable particle. In some embodiments, the particles have the further advantage that they are soluble, e.g. in water and a range of organic solvents, and can be used in a variety of homogeneous application formats.

Accordingly, in a first aspect, the present invention provides a particle comprising a core, such as a metallic core, linked to a plurality of ligands, wherein the ligands comprise a carbohydrate group. The ligands may comprise the carbohydrate groups alone or in combination with peptides, protein domains, nucleic acid segments or fluorescent groups.

In a further aspect, the present invention provides compositions comprising populations of one or more of the above defined particles. In some embodiments, the populations of nanoparticles may have different densities of the same or different ligands attached to the core.

In a further aspect, the present invention provides the above defined particles for use in a method of medical treatment.

In a further aspect, the present invention provides the use of the above defined particles for the preparation of a medicament for the treatment of a condition ameliorated by the administration of the ligand. By way of example, this may occur as the ligand blocks a carbohydrate mediated interaction that would otherwise tend to lead to a pathology.

In this embodiment, the present invention has advantages over prior art approaches for treating conditions involving carbohydrate mediated interactions. As described above, typically the interactions are polyvalent whereas the agent used to treat the interactions are often only capable of modulating one or a few of the these interactions. This has the result that it is difficult to deliver an agent to the site of the interaction which is capable of reliably modulating the interaction for the desired therapeutic effect. In contrast to this problem, the present invention provides agents having a plurality of ligands for modulating the carbohydrate mediated interactions, potentially overcoming the difficulty in modulating the polyvalent interactions.

In preferred embodiments, the mean diameter of the core, preferably the metallic core, is between 0.5 and 100 nm, more preferably between 1 and 50 nm, and still more preferably between 1 and 20 nm. The mean diameter can be measured using techniques well known in the art such as transmission electron microscopy.

The core material can be a metal or semiconductor and may be formed of more than one type of atom. Preferably, the core material is a metal selected from Au, Ag or Cu. Nanoparticles cores formed from alloys have also been reported, including Au/Ag, Au/Cu, Au/Ag/Cu, Au/Pt, Au/Pd and Au/Ag/Cu/Pd, and may be used in the present invention. Preferred core materials are Au and Ag, with the most preferred material being Au. Where gold clusters are used, they will preferably have between about 100 and 500 gold atoms to provide core diameters in the nanometre range. Other particularly useful core materials are or are doped with one or more atoms that are NMR active, allowing the nanoparticles to be detected using NMR, both in vitro and in vivo. Examples of NMR active atoms include gadolinium and europium.

Nanoparticle cores comprising semiconductor atoms can be detected as nanometre scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide.

The nanoparticles and the results of their interactions can be detected using a number of techniques well known in the art. These can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance, that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles includes or is doped with atoms which are NMR active then this technique can be used to detect the particles, both in vitro or in vivo, using techniques well known in the art. Nanoparticles can also be detected as described in [18], using a system based on quantitative signal amplification using the nanoparticle-promoted reduction of silver (I) and using a flatbed scanner as a reader. Fluorescence spectroscopy can be used if the nanoparticles include ligands combining carbohydrate groups and fluorescent probes. Also, isotopic labelling of the carbohydrate can be used to facilitate their detection.

The ligand linked to the core comprises one or more carbohydrate (saccharide) groups, e.g. comprising a polysaccharide, an oligosaccharide or a single saccharide group. The ligand may be also be a glycanoconjugate such as a glycolipid or a glycoprotein. In addition to the carbohydrate group, the ligand may additionally comprises one or more of a peptide group, a protein domain, a nucleic acid molecule (e.g. a DNA segment) and/or a fluorescent probe.

The particles may have more than one species of ligand immobilised thereon, e.g. 2, 3, 4, 5, 10, 20 or 100 different ligands. Alternatively or additionally a plurality of different types of particles can be employed together.

In preferred embodiments, the mean number of ligands linked to an individual metallic core of the particle is at least 20 ligands, more preferably at least 50 ligands, and most preferably at least 100 ligands. Preferred densities of ligands are in the ranges of 70-100 ligands per 200 gold atoms as determined by elemental analysis.

Preferably, the ligands are attached covalently to the core of the particles. Protocols for carrying this out are known in the art, although the work described herein is the first report of the reactions being used to covalently bond carbohydrate ligands to the core of the particle. This may be carried out by reacting ligands with reductive end groups with gold under reducing conditions. A preferred method of producing the particles employs thiol derivatised carbohydrate moieties to couple the ligands to particles. Thus, in one aspect, the present invention provides a method of preparing the above defined particles, the method comprising:

synthesizing a sulphide derivative of the ligand;
reacting the sulphide derivatised ligand and tetrachloroauric acid in the presence of reducing agent to produce the particles.

In a preferred embodiment, the ligand is derivatised as a protected disulphide. Conveniently, the disulphide protected ligand in methanol can be added to an aqueous solution of tetrachloroauric acid. A preferred reducing agent is sodium borohydride. Other preferred features of the method are described in the examples below.

The present invention provides a way of presenting a spherical array of carbohydrate-containing ligands having advantages over other types of array proposed in the prior art. In particular, the nanoparticles are soluble in most organic solvents and especially water. This can be used in their purification and importantly means that they can be used in solution as macroarrays for presenting the ligand immobilised on the surface of the particle. The fact that the nanoparticles are soluble has the advantage of presenting the carbohydrates in a natural conformation. For therapeutic applications, the nanoparticles are non-toxic, soluble and excreted in the urine.

A range of different carbohydrate mediated interactions are known in the art and could be studied or modulated using the nanoparticles disclosed herein. These include leukocyte-endothelial cell adhesion, carbohydrate-antibody interactions, carbohydrate-protein bacterial and viral infection, immunological recognition of tumour cells, tumour cells-endothelial cells (e.g. to study metastasis) and foreign tissue and cell recognition. The following examples of application for the nanoparticles are provided by way of illustration and not limitation to support the wide applicability of the technologies described herein.

In general, it has been a difficult problem in the art to detect or modulate carbohydrate-mediated interactions since the binding of carbohydrates to other species such as proteins or other carbohydrates is very weak and tends to be polyvalent. Thus, for detection the binding is weak and for modulating interaction, monovalent agents have only had a limited success in disrupting polyvalent carbohydrate based interactions.

In embodiments of the invention relating to carbohydrate-carbohydrate interactions, two types of interaction can be identified. In homophilic interactions, identical carbohydrates interact with one another and could be detected by steadily increasing the concentration of particles having a single species of ligands immobilised on their surface until aggregation occurs. This may be detected by light scattering or electronic effects. Heterophilic interactions can be detected by mixing together two or more different nanoparticles and determining the aggregation state of the particles.

Thus, the present invention provides a versatile platform for studying and modulating carbohydrate-mediated interactions. For example, the particles could be used to detect anti-carbohydrate antibodies, detecting the binding of antibody to the ligands on the particle via light scattering to pick up aggregation of the particles, or electric field effects, such as surface plasmon resonance, which would be modified when the metal atoms in the particles cluster together.

In one example of this aspect of the invention, the nanoparticles can be employed to type blood groups, as commonly carried out in medicine to match compatible donors and recipients for blood transfusion. Blood groups arise as common gut bacteria bear carbohydrate antigens which are similar or identical to blood group antigens present on the surface of red blood cells, and these bacterial antigens stimulate the production of antibodies in individuals who do not bear the corresponding antigen on their own red blood cells. Thus, sera from an individual is tested for antibodies that agglutinate the red blood cells of the donor and vice versa in a cross-match test to detect the potentially harmful antibodies in the recipient. At present, blood typing is carried out using these agglutination tests which are inconvenient and not readily susceptible to automation or high throughput.

The blood group antigens are carbohydrates, e.g. for the common antigen:

| Type O | R-GlcNAc-Gal(Fuc) |
| Type A | R-GlcNAc-Gal(Fuc)-GalNAc |
| Type B | R-GlcNAc-Gal(Fuc)-Gal |
| Type AB | Type A and Type B antigens |

Therefore, populations of nanoparticles can be made having blood group antigens immobilised on their surface. Thus, if a sample contained sera capable of binding to the blood group antigen, then adding the nanoparticle to a sample from a patient would allow the blood type of donors and recipients to be determined.

Another application of the nanoparticles is to modulate inflammation. In particular, members of the selectin family participate in the initial attachment of white blood cells (leukocytes) to endothelial cells during the process of leukocyte recruitment to inflamed tissues. L-selectin is expressed on leukocytes, P-selectin on platelets and E-selectin on endothelial cells. E-selectin and P-selectin are induced on endothelial cells in response to pro-inflammatory cytokines and bind to ELAM receptors on the surface of endothelial cells. L-selectin is constitutively expressed on circulating leukocytes and binds to glycoproteins uniquely expressed on the activated endothelium. Thus, all of these interactions could be employed as therapeutic targets for modulating inflammation, and in particular reduce aberrant inflammation.

Prior art approaches to employing selectins as therapeutic targets have been based on the fact that the selectins share a common calcium dependent lectin domain which can be targeted by carbohydrate based ligands. Prior art screening has found that all three selectins bind to the sialylated and fucosylated tetrasaccharide sialyl Lewis X (sLe$^x$) and that this molecule and analogues thereof can bind to selectin, albeit weakly. The prior art approaches suffer from the problem that the interaction of sLe$^x$ and selectin is weak and the interaction of the cells expressing the selectin is polyvalent. Accordingly, in one of its aspects, the present invention proposes a treatment of inflammation using nanoparticles having one or more selectin ligands immobilised thereon. A discussion of selectin mediated inflammation and compounds that can be used to modulate the interaction is provided in [5b].

In a further aspect, nanoparticles in which the carbohydrate (saccharide) group is an antigen can be administered as a vaccine, e.g. ballistically, using a delivery gun to accelerate their transdermal passage through the outer layer of the epidermis. The nanoparticles can then be taken up, e.g. by dendritic cells, which mature as they migrate through the lymphatic system, resulting in modulation of the immune response and vaccination against the saccharide antigen, as described in [19].

In a further application, it is known that cell surface carbohydrates act as ligands for viral or bacterial receptors (called adhesins) and that binding of the carbohydrates to the receptors is an event required during infection. Synthetic carbohydrates, e.g. glycoconjugates, that are capable of modulating these interactions can be immobilised in the nanoparticles of the invention and used as reagents to study these interactions and as therapeutics to prevent viral or bacterial infection. One example of a carbohydrate ligand mediating bacterial infection is *Helicobacter pylori* which causes chronic active gastritis, gastric and duodenal ulcers, gastric adenocarcinoma and mucosa-associated lymphoid tissue lymphoma in humans. As the cell specific attachment of *H. pylori* can occur via multiple carbohydrates including Lewis b antigen, sialylated oligosaccharides and sulphated mucin glycoproteins, nanoparticles capable of modulating (i.e. blocking) the different adhesin interactions could be used as treatments of the above conditions.

Examples of viral infections mediated by carbohydrates include the influenza virus which infects cells via the multivalent binding of hemaglutinin molecules on the viral envelope to sialic acid terminated host glycoconjugates. Thus, by infection may be inhibited by disrupting this event.

HIV-1 also infects cells by recognising cell surface carbohydrate structures and the glycolipid galactosylceramide (GalCer) has been identified as a ligand for the HIV-1 receptor gp120. Thus, GalCer or analogues thereof could be immobilised on the surface of nanoparticles and used to inhibit the interaction of cellular GalCer and HIV-1.

In a further application, the present invention may be useful in the modulation of immune response, e.g. following transplantation. As the immunological recognition of tissue begins with carbohydrate mediated interactions between surface carbohydrates present on transplanted tissue and the components of the host's immune system such as antibodies, so this can be targeted to ameliorate immune reactions that result from this interaction. By way of example the carbohydrate Galα1-3Galβ1-4GlnAc (the 'αGal' epitope) has been implicated as an important antigenic epitope involved in the rejection of transplanted tissue. Thus, modulation of the interaction of the αGal epitope and the immune system may be a therapeutic target for the nanoparticles described herein.

An alternative approach may be useful in the treatment of cancer as many tumour associated antigens or tumour autocrine factors are carbohydrate based. In this event, the nanoparticles could be provided as vaccines prime the immune system to produce antibodies which are capable of attacking tumour cells presenting the carbohydrates on their surface. In this regard, it is known that many tumour cells possess aberrant glycosylation patterns which may enable the immune response stimulated by nanoparticles to be directed specifically to tumour cells as opposed to normal, healthy cells. The nanoparticles can also be used to inhibit metastatis in cancer, e.g. through the migration of tumour cells through the endothelial cells.

In a further aspect, the nanoparticles can be used as carriers to raise antibodies capable of specifically binding the ligand. This is particularly advantageous as it can be a challenging problem in the art to raise antibodies against carbohydrates-containing moieties as they are often small and do not cause strong immune responses.

In a further aspect, the present invention provides a method of determining whether a carbohydrate mediated interactions occurs, the method comprising contacting one or more species of nanoparticles with a candidate binding partner and determining whether binding takes place.

In a further aspect, the present invention provides a method of screening for substances capable of binding to a ligand comprising a carbohydrate group, the method comprising:
contacting particles comprising a metallic core linked to a plurality of the ligands with one or more candidate compounds; and
detecting whether the candidate compounds binds to the ligand.

In a further aspect, the present invention provides a method of determining the presence in a sample of a substance capable of binding to a ligand comprising a carbohydrate ligand, the method comprising contacting the sample with nanoparticles linked to the ligand and determining whether binding takes place. The method may be used to determine the presence or amount of one or more analytes in a sample, e.g. for use in assisting the diagnosis of a disease state associated with the presence of the analyte.

In a further embodiment, the nanoparticles can be employed to study or detect carbohydrate mediated interactions in conjunction with species immobilised on solid surfaces, for example ligands immobilised on gold surfaces as described in [6a]. These species might be other carbohydrates, candidate binding partners or analytes.

In a further aspect, carbohydrates can be attached to nanocrystals of cadmium selenide to provide quantum dots, which can then be guided to the required cellular structure by nanoparticles. As discussed in [20], quantum dots have potential uses in biological imaging, in both electronic and optical devices, quantum computers and the screening of candidate drugs.

Embodiments of the present invention will now be described by way of example and not limitation with reference to the accompanying figures.

BRIEF DESCRIPTION OF THE FIGURES

FIG. 3 shows $^1$H NMR spectra of: (A) 2-Au in $D_2O$ (a); 2 in $D_2O$ (b) and 2 in $CD_3OD$ (c) and (B) 3-Au in $D_2O$ (a); 3 in $D_2O$ (b) and 3 in 70% $CD_3OD/D_2O$ (c)

DETAILED DESCRIPTION

Pharmaceutical Compositions

The nanoparticles described herein or their derivatives can be formulated in pharmaceutical compositions, and administered to patients in a variety of forms, in particular to treat conditions ameliorated by the administration of the ligand. By way of example, this may occur as the ligand blocks a carbohydrate mediated interaction that would otherwise tend to lead to a pathology. Thus, the nanoparticles may be used as medicament for modulating leukocyte-endothelial cell adhesion, carbohydrate-antibody interactions, carbohydrate-protein bacterial and viral infection, immunological recognition of tumour cells, the inhibition of metastatis and foreign tissue and cell recognition.

Pharmaceutical compositions for oral administration may be in tablet, capsule, powder or liquid form. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicizing agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. By way of example, and the compositions are preferably administered to patients in dosages of between about 0.01 and 100 mg of active compound per kg of body weight, and more preferably between about 0.5 and 10 mg/kg of body weight.

Antibodies

The nanoparticles may be used as carriers for raising antibody responses against the carbohydrate containing ligands linked to the core particles. These antibodies can be modified using techniques which are standard in the art. Antibodies similar to those exemplified for the first time here can also be produced using the teaching herein in conjunction with known methods. These methods of producing antibodies include immunising a mammal (e.g. mouse, rat, rabbit, horse, goat, sheep or monkey) with the nanoparticle(s). Antibodies may be obtained from immunised animals using any of a variety of techniques known in the art, and screened, preferably using binding of antibody to antigen of interest. Isolation of antibodies and/or antibody-producing cells from an animal may be accompanied by a step of sacrificing the animal.

As an alternative or supplement to immunising a mammal with a nanoparticle, an antibody specific for the ligand and/or nanoparticle may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the nanoparticles, or may be one constructed using sequences obtained from an organism which has been exposed to the antigen of interest.

The term "monoclonal antibody" as used herein refers to an antibody obtained from a substantially homogenous population of antibodies, i.e. the individual antibodies comprising the population are identical apart from possible naturally occurring mutations that may be present in minor amounts. Monoclonal antibodies can be produced by the method first described by Kohler and Milstein, Nature, 256:495, 1975 or may be made by recombinant methods, see Cabilly et al, U.S. Pat. No. 4,816,567, or Mage and Lamoyi in Monoclonal Antibody Production Techniques and Applications, pages 79-97, Marcel Dekker Inc, New York, 1987.

In the hybridoma method, a mouse or other appropriate host animal is immunised with the antigen by subcutaneous, intraperitoneal, or intramuscular routes to elicit lymphocytes that produce or are capable of producing antibodies that will specifically bind to the nanoparticles used for immunisation. Alternatively, lymphocytes may be immunised in vitro. Lymphocytes then are fused with myeloma cells using a suitable fusing agent, such as polyethylene glycol, to form a hybridoma cell, see Goding, Monoclonal Antibodies: Principles and Practice, pp. 59-103 (Academic Press, 1986).

The hybridoma cells thus prepared can be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody producing cells, and are sensitive to a medium such as HAT medium.

Culture medium in which hybridoma cells are growing is assayed for production of monoclonal antibodies directed against the nanoparticles/ligands. Preferably, the binding specificity is determined by enzyme-linked immunoabsorbance assay (ELISA). The monoclonal antibodies of the invention are those that specifically bind to the nanoparticles/ligands.

In a preferred embodiment of the invention, the monoclonal antibody will have an affinity which is greater than micromolar or greater affinity (i.e. an affinity greater than $10^{-6}$ mol) as determined, for example, by Scatchard analysis, see Munson & Pollard, Anal. Biochem., 107:220, 1980.

After hybridoma cells are identified that produce neutralising antibodies of the desired specificity and affinity, the clones can be subcloned by limiting dilution procedures and grown by standard methods. Suitable culture media for this purpose include Dulbecco's Modified Eagle's Medium or RPMI-1640 medium. In addition, the hybridoma cells may be grown in vivo as ascites tumours in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Nucleic acid encoding the monoclonal antibodies of the invention is readily isolated and sequenced using procedures well known in the art, e.g. by using oligonucleotide probes that are capable of binding specifically to genes encoding the heavy and light chains of murine antibodies. The hybridoma cells of the invention are a preferred source of nucleic acid encoding the antibodies or fragments thereof. Once isolated, the nucleic acid is ligated into expression or cloning vectors, which are then transfected into host cells, which can be cultured so that the monoclonal antibodies are produced in the recombinant host cell culture.

Hybridomas capable of producing antibody with desired binding characteristics are within the scope of the present invention, as are host cells containing nucleic acid encoding antibodies (including antibody fragments) and capable of their expression. The invention also provides methods of production of the antibodies including growing a cell capable of producing the antibody under conditions in which the antibody is produced, and preferably secreted.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope, here a carbohydrate ligand as defined herein.

Examples of antibody fragments, capable of binding an antigen or other binding partner, are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and $F(ab')_2$ fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies, humanised antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

Experimental

As strategy for tailoring polyvalent carbohydrate surfaces with globular shapes to investigate in solution carbohydrate-to-carbohydrate recognition, an approach was devised by which carbohydrates are linked to gold nanoparticles [7]. By way of example, the preparation, characterisation and preliminary interaction studies of sugar functionalized monolayer and water soluble gold nanoclusters is disclosed below. Thiol derivatised neoglycoconjugates of two biological significant oligosaccharides, the lactose disaccharide (Galβ(1-4)Glcβ1-OR) 1 and 2 and of the trisaccharide Le$^x$ antigen:

(Galβ(1-4)[Fucα(1-3)]GlcNAcβ1-OR) 3 have been prepared to attach them to gold nanoparticles. The trisaccharide Le$^x$ and the disaccharide lactose build up the glycosphingolipid (GSL) Le$^x$ antigen:

(Galβ(4)[Fucl-3]GlcNAcβ1-3Galβ1-4Glcβ1-OCer)

which have been proposed to mediate morula compaction and metastasis in healthy and carcinoma mouse cells respectively, via a homotypic carbohydrate-to-carbohydrate interaction. [8]

The lacto and Le$^x$ protected glyconanoparticles provide a glycocalyx-like surface with chemically well defined synthetic matrix and globular shape. Moreover, this approach opens the way to tailor glyconanoparticles containing a variety of carbohydrate ligands as well as different surface density providing an under-control model for structure-function studies and for investigating carbohydrate clustering) and orientation effects at a surface. [10] The lacto- and Le$^x$ functionalised nanoparticles will be our polyvalent model system to mimic GSL clustering in plasma membrane [11] and to investigate in solution the attractive and repulsive forces involved in cell aggregation via carbohydrate-to-carbohydrate interactions. Previous studies using synthetic receptors provided first solid evidence that stabilising interactions between lipophilic carbohydrate surfaces exist in water. [12]

Figure 1:
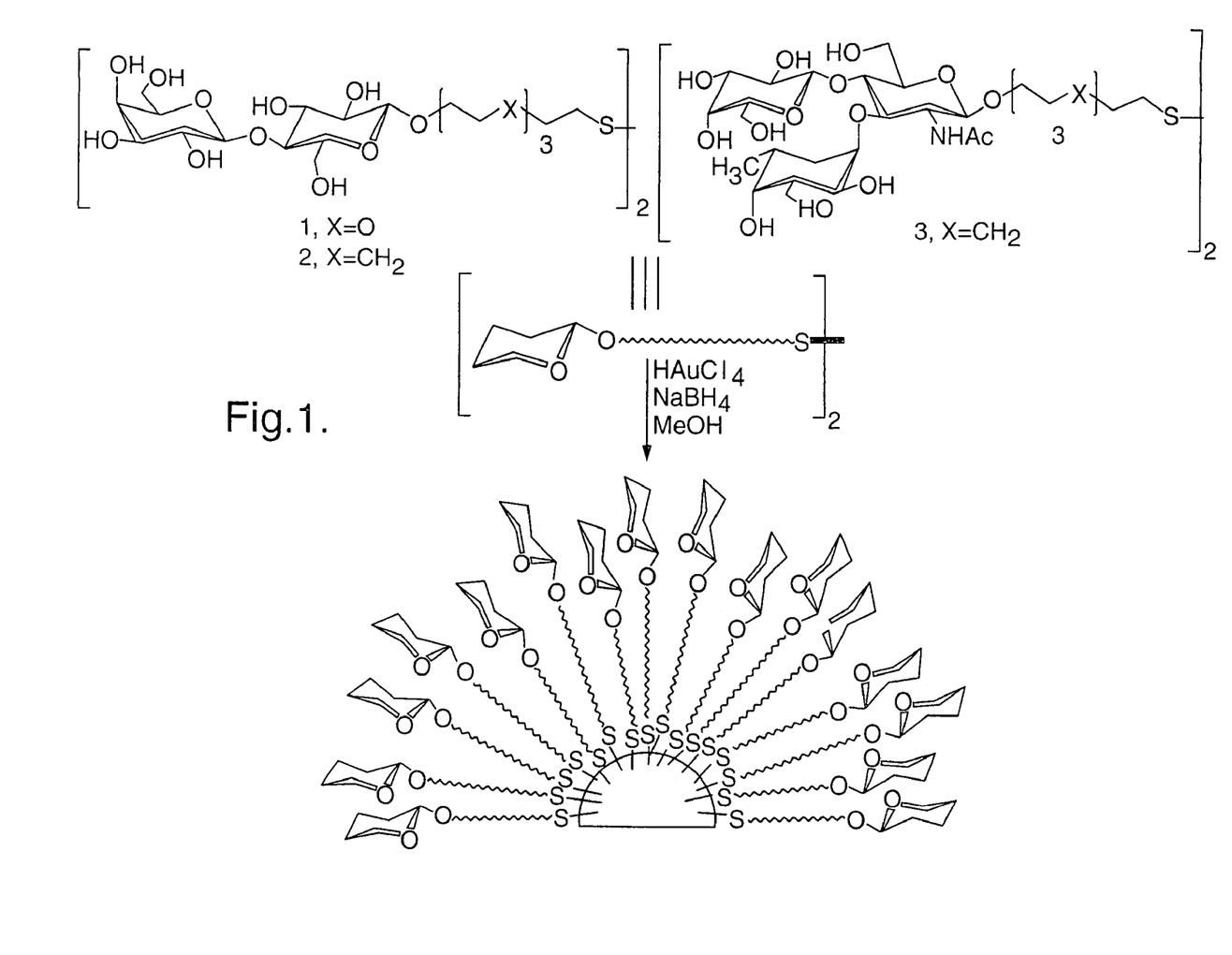
FIG. 1 shows schematically the method used to synthesise the nanoparticles.

The synthesis of the disulfides 1, 2 and 3 was carried out by glycosidation of the conveniently protected lactose and Le$^x$ derivative with 11-thioacetate-3,6,9-trioxa-undecanol (for 1) and 11-thioacetate undecanol (for 2 and 3) using the trichloroacetimidate method, see FIG. 1. [13] Compounds 1, 2 and 3 were isolated as disulfide forms, and in this form used for the formation of the gold protected glyconanoparticles. The water soluble glyconanoparticles 1-Au, 2-Au and 3-Au were obtained in methanol following the procedure of Brust et al for the synthesis of monolayer protected gold nanoclusters. [7a] A series of gold protected nanoparticles, all of them soluble in organic solvents, have recently been prepared for different purposes. [14] The lacto-Au and Le$^x$-Au glyconanoparticles are water soluble, stable and can be manipulated as a water soluble biological macromolecules. They have been purified by dialysis and characterised by $^1$H-NMR, UV and transmission electron microscopy (TEM).

Synthesis of glyconanoparticles: A solution of disulphide 1,2, or 3 (0.012M, 5.5 eq) in MeOH was added to a solution of tetrachloroauric acid (0.025M, 1 eq) in water. NaBH$_4$ (1M, 22 eq) in water was added in small portions with rapid stirring. The black suspension that was formed was stirred for additional 2 hours and the solvent was then removed under vacuum. The crude of the reaction was washed with MeOH and was centrifuged for 10 minutes. The methanol was removed and the process was repeated several times until the starting material was not detected by TLC. The glyco-nanoparticles are completely insoluble in MeOH but quite soluble in water. They were purified by dialysis: 50 mg of crude product was dissolved in 10 mL of water (NANOpure). This solution was loaded into 10 cm segments of cellulose ester dialysis membrane (SIGMA, MWCO=12400) and placed in 4 L of water (NANOpure). The dark glyconanoparticles solution was collected from the dialysis segments and lyophilized. The products obtained were free of salts and starting material (absence of signals due to disulphide and Na$^+$ in NMR).

Transmission Electron Microscopy (TEM) examination of the samples was carried out with a Philips CM200 microscope working at 200 kV. A single drop of a 0.1 mg/ml aqueous solution of the gold glyconanoparticles was placed onto a copper grid coated with a carbon film. The grid was left to dry in air for several hours at room temperature. Particle size distribution of the Au clusters were evaluated from several micrographs using an automatic image analyser. The number of particles selected for consideration was around 400, which resulted in stable size distribution statistic.

Figure 2:
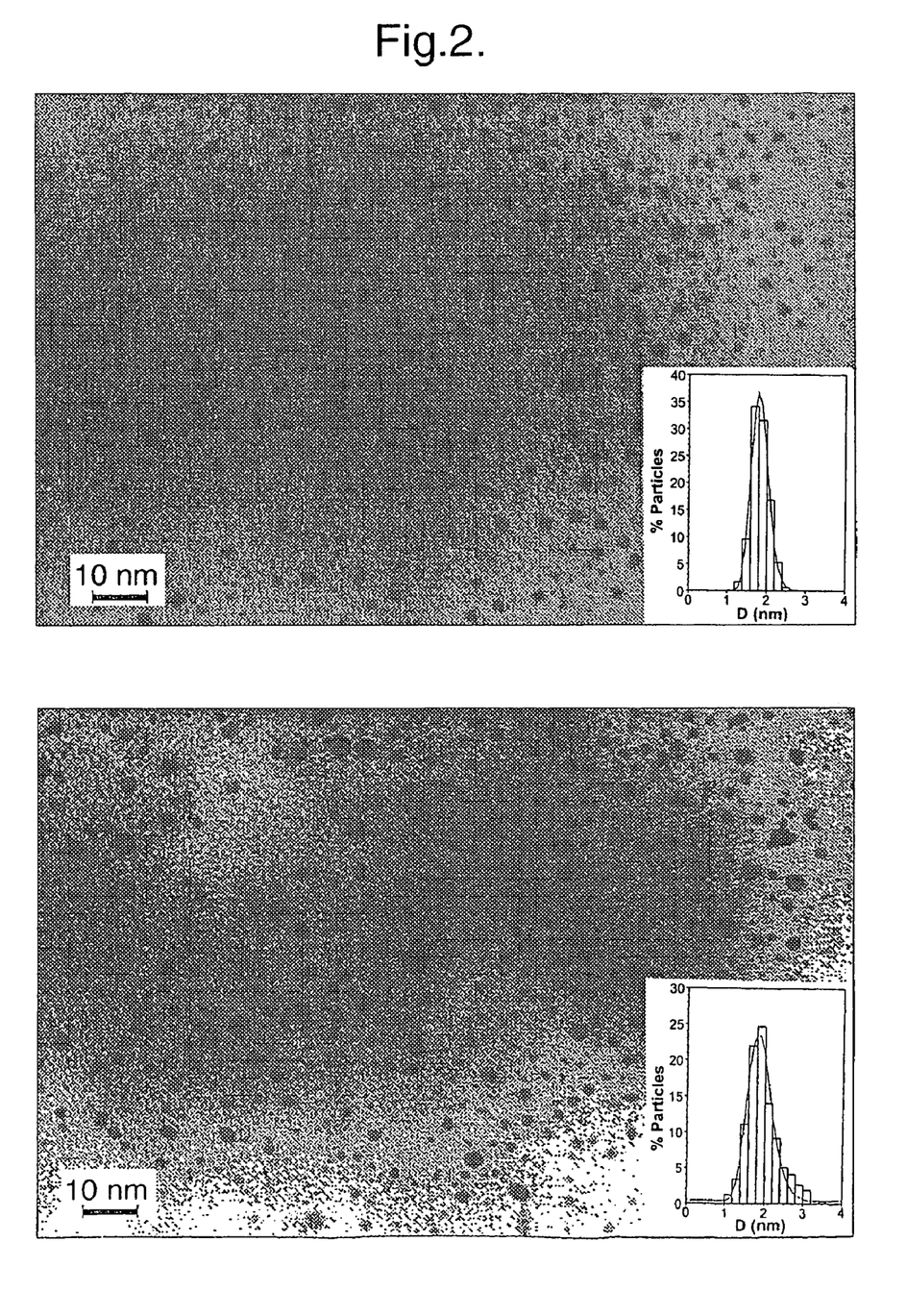
FIG. 2 shows transmission electron micrographs and core size distribution histograms (insets) of the lacto 2-Au (top) and the Le$^x$ 3-Au (bottom) glyconanoparticles.

FIG. 2 shows TEM images and core size distribution histograms for the 2-Au and 3-Au gold glyconanoparticles. The gold particles stabilized with the lactose show a narrower and more homogeneous particle size distribution than the particles stabilized with the Le$^x$ conjugate. A mean diameter of 1.8 nm was found in both samples for the gold core of the functionalized nanoparticles. Such a mean particle size corresponds, according to previous work, [15] to an average number of gold atoms per particles of ca. 200 and 70 protecting alkanethiolate glycoconjugates. The aqueous solutions of the nanoparticles were stable during months and no agglomeration was detected by TEM. The presentation of the carbohydrate molecules at the nanoparticles surface was then investigated. The molecular properties of the neoglycoconjugates 1, 2 and 3 suffer a differential change after attaching them to the gold surface. For example, the lacto derivative 2, which is soluble in methanol and insoluble in water, gives glyconanoparticles 2-Au insoluble in methanol but with good solubility in water. The Le$^x$ derivative 3 is soluble in methanol and water, its nanoparticle 3-Au, however, is insoluble in methanol and very soluble in water. These differences in solubility can be used to purify the glyconanoparticles from the non-reacted disulfides by washing them with methanol. However, the most significant fact in these changes is that they reveal the influence of clustering at the surface on the carbohydrate presentation to the surrounding.

Figure 3A:
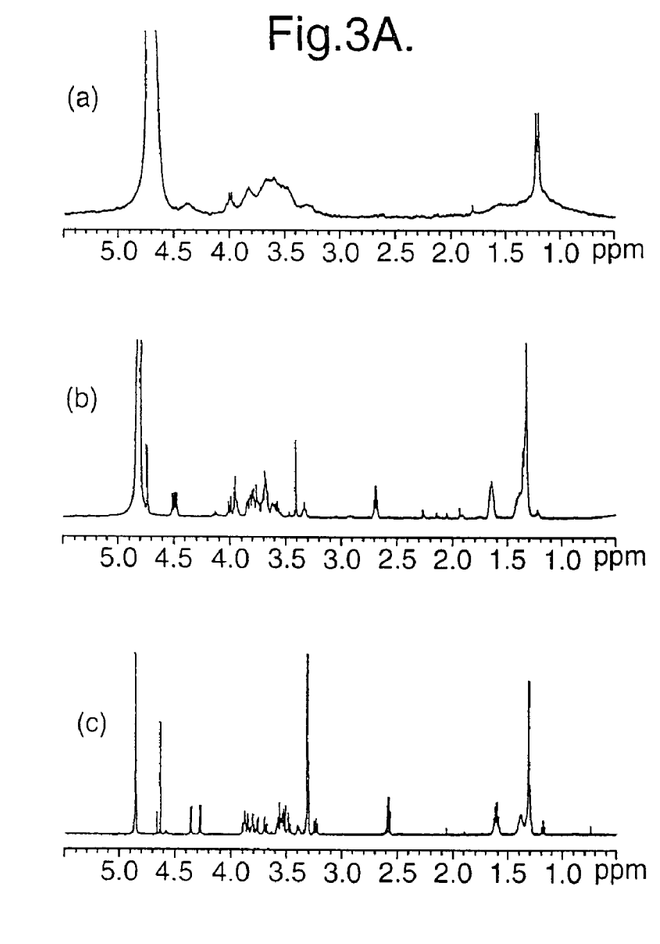
Figure 3B:
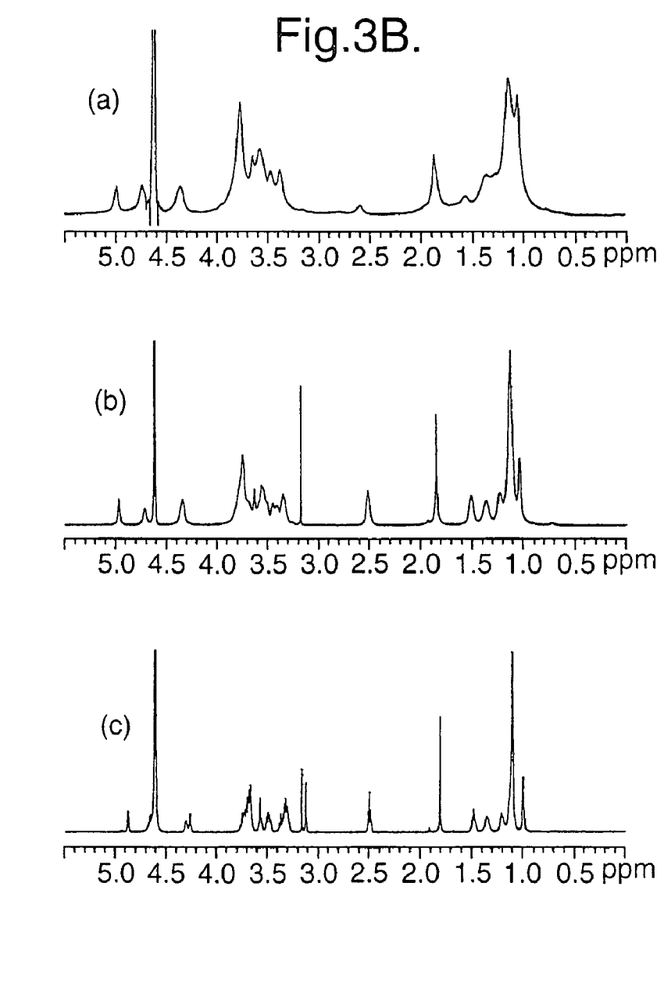

The $^1$H-NMR spectra of the glyconanoparticles show clearly these differences (FIG. 3). The spectra of the lacto-nanoparticles 1-Au and 2-Au in D$_2$O differ strongly from those of the lacto-disulfides 1 and 2 (FIG. 3A spectrum of 1 not shown) showing the line broadening of slowly rotating macromolecules in solution. The signal of the methylenes closest to the thiolate/Au interface completely disappears, as it occurs in the alkanethiol monolayer-protected gold nanoclusters. In contrast, these differences are not founded in the case of the 3-Au nanoparticles. The $^1$H-NMR spectra in $D_2O$ of both 3 and 3-Au show similar broadening for all signals (FIG. 3B, a, b), indicating an intramolecular aggregation already present in the Le$^x$ disulfide 3. This self-interaction persists even at highly diluted water solution and is abolished by addition to the $D_2O$ solution of 3 of increasing amounts of $CD_3OD$. Some well-resolved signals appear in $CD_3OD/D_2O$ (1:1) solution and in 70% $CD_3OD/D_2O$ solution all signal are well-resolved in the spectrum (FIG. 3B, c). The tendency of the Le$^x$ disulfide 3 to self-assemble in water cannot exclusively be attributed to the hydrophobicity of the aliphatic chain, but rather to the specific partaking of the carbohydrate moiety in this aggregation, as point out the lack of aggregation in water observed in the $^1$H-NMR of the lacto-disulfides 1 and 2 (FIG. 3A). The self-aggregation ability will have consequences in the organisation and clustering of Le$^x$-containing GSLs, as claimed by some authors [16] and contrary to the proposal of others that the carbohydrate head group plays an insignificant role in formation of glycolipid-enriched microdomains in the plasma membrane. [17]

The steric crowding of the carbohydrate moiety at the nanoparticle surfaces is also shown by the different behaviour of 1 and 2 and their corresponding nanoclusters 1-Au and 2-Au with β-glycosidases. The β-galactosidase of *E. coli* processes 1 and 2 at a level comparable to lactose itself (5-10% relative to the specific activity of GONP), while the hydrolysis by the enzyme under the same conditions of 1-Au and 2-Au nanoparticles was barely detected (<3% relative to the enzymatic activity with the free ligands 1 and 2).

These experiments demonstrate that it is possible to use nanoparticles to produce tailored globular carbohydrate models mimicking GSL-clusters in plasma membrane, allowing for the first time investigations to be carried out in solution of a novel mechanism of cell adhesion via carbohydrate-to-carbohydrate interactions. The glyconanoparticle approach described herein provides a strategy to prepare, in a simple way, a great variety of globular carbohydrate arrays that can advantageously compete with other spherical (dendrimers, liposome) or linear carbohydrate displays. The lacto- and Le$^x$-nanoparticles may be considered appropriate models to intervene in cell-cell adhesion and recognition processes.

REFERENCES

The references mentioned herein are all expressly incorporated by reference.

[1] a) G. I. Bell, M. Dembo, P. Bongrand, *Biophys. J.* 1984, 45, 1051-1064; b) A. Frey, K. T. Giannasca, R. Weltzin, P. J. Giannasca, H. Reggio, W. I. Lencer, M. R. Neutra, *J. Exp. Med.* 1996, 184, 1045-1059.
[2] W. I. Weis, K. Drickamer, *Annu. Rev. Biochem.* 1996, 65, 441-73.
[3] a) S. Hakomori, *Pure & Appl. Chem.* 1991, 63, 473-482; b) G. N. Misevic, *Microsc. Res. Tech.* 1999, 44, 304-309 and references therein.
[4] M. Mammen, S. Choi, G. M. Whitesides, *Angew. Chem. Int. Ed.* 1998, 37, 2754-2794.
[5] a) L. Kiessling, N. L. Pohl, *Chemistry & Biology* 1996, 3, 71-77; b) K. J. Yarema, C. R. Bertozzi, *Curr. Opin. Chem. Biol.* 1998, 2, 62-66; c) P. I. Kitov, J. M. Sadowska, G. Mulvey, G. D. Armstrong, H. Ling, N. S. Pannus, R. J. Read, D. R. Bundle, *Nature* 2000, 403, 669-672.
[6] a) B. T. Houseman, M. Mrksich, Angew. *Chem. Int. Ed.* 1999, 38, 782-785; b) N. Horan, L. Yan, H. Isobe, G. M. Whitesides, D. Kahne, *Proc. Natl. Acad. Sci. USA* 1999, 96, 11782-11786.
[7] a) M. Brust, J. Fink, D. Bethell, D. J. Schiffrin, C. Kiely, *J. Chem. Soc., Chem. Commun.* 1995, 1655-1656; b) A. C. Templeton, W. P. Wuelfing, R. W. Murray, *Acc. Chem. Res.* 2000, 33, 27-36; c) J. J. Storhoff, C. A. Mirkin, *Chem. Rev.* 1999, 99, 1849-1862.
[8] I. Eggens, B. Fenderson, T. Toyokuni, B. Dean, M. Stroud, S. Hakomori, *J. Biol. Chem.* 1989, 264, 9476-9484.
[9] a) P. H. Weigel, R. L. Schnaar, M. S. Kuhlenschmidt, E. Schmell, R. T. Lee, Y. C. Lee, S. Roseman, *J. Biol. Chem.* 1979, 254, 10830-10838; b) R. Liang, J. Loebach, N. Horan, M. Ge. C. Thompson, L. Yan, D. Kahne, *Proc. Natl. Acad. Sci. USA* 1997, 94, 10554-10559.
[10] N. Strömberg, P.-G. Nyholm, I. Pascher, S. Normark, *Proc. Natl. Acad. Sci. USA* 1991, 88, 9340-9344.
[11] S. Hakomori, K. Handa, K. Iwabuchi, S. Yamamura, A. Prinetti, *Glycobiology* 1998, 8, xi-xix.
[12] a) J. M. Coterón, C. Vicent, C. Bosso, S. Penadés, *J. Am. Chem. Soc.* 1993, 115, 10066-10076; b) J. Jiménez-Barbero, E. Junquera, M. Martin-Pastor, S. Sharma, C. Vicent, S. Penadés, *J. Am. Chem. Soc.* 1995, 117, 11198-11204; c) J. C. Morales, D. Zurita, S. Penadés, *J. Org. Chem.* 1998, 63, 9212-9222.
[13] R. R. Schmidt, K.-H. Jung in *Preparative Carbohydrate Chemistry*, (Ed. Stephen Hanessian), Marcel Dekker Inc. 1997, pp 283-312. The synthesis of the neoglycoconjugates 1,2 and 3 will be published elsewhere.
[14] a) D. Fitzmaurice, S. Nagaraja Rao, J. A. Preece, J. F. Stoddart, S. Wenger, N. Zaccheroni, *Angew. Chem. Int. Ed.* 1999, 38, 1147-1150; b) J. Liu, S. Mendoza, E. Román, M. J. Lynn, R. Xu, A. E. Kaifer, *J. Am. Chem. Soc.* 1999, 121, 4304-4305; c) A. K. Boal, F. Iihan, J. E. DeRouchey, T. Thurn-Albrecht, T. P. Russell, V. M. Rotello, *Nature* 2000, 404, 746-748.
[15] A. C. Templeton, S. Chen, S. M. Gross, R. W. Murray, *Langmuir* 1999, 15, 66-76.
[16] K. Simon, E. Ikonen, *Nature* 1997, 387, 569-572.
[17] D. A. Brown, E. London, *Biochem. Biophys. Res. Commun.* 1997, 240, 1-7.
[18] Taton et al, Science, 289:1757-1760, 2000.
[19] G. Ada, N. Engl. J. Med., 345(14), 1042-1053, 2001.
[20] E. Klarreich, Nature, 413, 450-452, 2001.

The invention claimed is:

1. A nanoparticle comprising a core of metal atoms covalently linked to at least 20 ligands, wherein the nanoparticle has more than one species of ligand immobilized thereon and wherein at least one of the species of ligand comprises a carbohydrate group.

2. A nanoparticle comprising a core of (a) metal atoms covalently linked to at least 20 ligands, wherein the ligands comprise carbohydrate groups and (b) semiconductor atoms.

3. The nanoparticle of claim 1 or 2, wherein the core is covalently linked to at least 50 ligands.

4. The nanoparticle of claim 1 or 2, wherein the core of the nanoparticle has a mean diameter between 0.5 and 100 nm.

5. The nanoparticle of claim 4, wherein metallic core comprises between about 100 and 500 Au atoms.

6. The nanoparticle of claim 1 or 2, wherein the metallic core comprises Au, Ag or Cu.

7. The nanoparticle of claim 1 or 2, wherein the core comprises an atom which is NMR active.

8. The nanoparticle of claim 7, wherein the NMR active atom is gadolinium and europium.

9. The nanoparticle of claim 1 or 2, wherein the core includes an atom which is capable of detection using surface plasmon resonance.

10. The nanoparticle of claim 1 or 2, wherein the ligands further comprise a label.

11. The nanoparticle of claim 10, wherein the label is a fluorescent group or a radioactive isotope.

12. The nanoparticle of claim 1 or 2, wherein the metallic core is an alloy selected from Au/Ag, Au/Cu, Au/Ag/Cu, Au/Pt, Au/Pd or Au/Ag/Cu/Pd.

13. The nanoparticle of claim 2, wherein the semiconductor atoms are capable of acting as a quantum dot.

14. The nanoparticle of claim 13, wherein the core is formed from cadmium selenide.

15. The nanoparticle of claim 1 or 2, wherein the ligands further comprise a peptide, a protein domain, a nucleic acid segment or a fluorescent group.

16. The nanoparticle of claim 1 or 2, wherein ligand comprises a polysaccharide, an oligosaccharide or a monosaccharide group.

17. The nanoparticle of claim 1 or 2, wherein the ligand comprises a glycanoconjugate.

18. The nanoparticle of claim 17, wherein the glycanoconjugate is a glycolipid or a glycoprotein.

19. The nanoparticle of claim 1, wherein the ligand is linked to the metallic core via a sulphide group.

20. The nanoparticle of claim 1 or 2, wherein the nanoparticle is water soluble.

21. A composition comprising a population of one or more of the nanoparticles of claim 1 or 2.

22. The composition of claim 21 which comprises a plurality of nanoparticles having different ligand groups.

23. A composition comprising a population of one or more of the nanoparticles of claim 1 or 2 for use in a method of medical treatment.

24. The nanoparticle of claim 1 or 2, wherein the core is covalently linked to at least 100 ligands.

25. The nanoparticle of claim 1 or 2, wherein the core has a mean diameter of between 1 and 20 nm.

26. The nanoparticle of claim 1 or 2, wherein the nanoparticle has more than one species of ligand immobilized thereon.

27. The nanoparticle of claim 26, wherein the nanoparticle has more than two species of ligand immobilized thereon.

28. The nanoparticle of claim 26, wherein the nanoparticle has more than five species of ligand immobilized thereon.

29. The nanoparticle of 26, wherein the further species of ligand comprises a peptide ligand, a protein domain ligand, a nucleic acid ligand or a fluorescent group ligand.

30. A method of preparing a nanoparticle comprising a metallic core covalently linked to a plurality of ligands, wherein the metallic core comprises gold atoms and the ligand comprises a carbohydrate group, the method comprising:

synthesizing a sulphide derivative of the ligand;

reacting the sulphide derivatised ligand and tetrachloroauric acid in the presence of reducing agent to produce the nanoparticles.

31. The method of claim 30, wherein the ligand is derivatised as a protected disulphide.

32. A nanoparticle as obtainable by the method of claim 30 or claim 31.

* * * * *

UNITED STATES PATENT AND TRADEMARK OFFICE
CERTIFICATE OF CORRECTION

| | |
|---|---|
| PATENT NO. | : 7,364,919 B2 |
| APPLICATION NO. | : 10/399284 |
| DATED | : April 29, 2008 |
| INVENTOR(S) | : Soledad Penades et al. |

It is certified that error appears in the above-identified patent and that said Letters Patent is hereby corrected as shown below:

Title Page, Item (73) Assignee, please add "Consejo Superior de Investigaciones Cientificas, Madrid (ES)."

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,364,919 B2  
APPLICATION NO. : 10/399284  
DATED : April 29, 2008  
INVENTOR(S) : Penades et al.

Page 1 of 1

It is certified that error appears in the above-identified patent and that said Letters Patent is hereby corrected as shown below:

Title Pg,

[*] Notice: Subject to any disclaimer, the term of this patent is extended or adjusted under 35 USC 154(b) by 535 days Delete the phrase "by 535 days" and insert -- by 680 days --

Signed and Sealed this

Twenty-eighth Day of July, 2009

JOHN DOLL  
*Acting Director of the United States Patent and Trademark Office*

UNITED STATES PATENT AND TRADEMARK OFFICE
CERTIFICATE OF CORRECTION

PATENT NO. : 7,364,919 B2 Page 1 of 1
APPLICATION NO. : 10/399284
DATED : April 29, 2008
INVENTOR(S) : Penades et al.

It is certified that error appears in the above-identified patent and that said Letters Patent is hereby corrected as shown below:

Title page. Item (*) Notice: delete "535 days" insert --680 days--.

Signed and Sealed this

Eleventh Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,364,919 B2 Page 1 of 1
APPLICATION NO. : 10/399284
DATED : April 29, 2008
INVENTOR(S) : Penades et al.

It is certified that error appears in the above-identified patent and that said Letters Patent is hereby corrected as shown below:

Title page. Item (*) Notice: delete "535 days" insert --580 days--.

This certificate supersedes the Certificates of Correction issued July 28, 2009 and August 11, 2009.

Signed and Sealed this

Eighth Day of September, 2009

David J. Kappos
*Director of the United States Patent and Trademark Office*